United States Patent
Hung (10) Patent No.: US 8,226,406 B2
(45) Date of Patent: Jul. 24, 2012

(54) POSITIONING ASSIST DEVICE FOR DRILLING MULTIPLE DENTAL IMPLANT HOLES

(75) Inventor: Yung-Tang Hung, Taoyuan County (TW)

(73) Assignee: Yung-Tang Hung, Taoyuan County (TW)

( * ) Notice: Subject to any disclaimer, the term of this patent is extended or adjusted under 35 U.S.C. 154(b) by 0 days.

(21) Appl. No.: 13/039,324

(22) Filed: Mar. 3, 2011

(65) Prior Publication Data
US 2011/0217668 A1    Sep. 8, 2011

(30) Foreign Application Priority Data
Mar. 5, 2010    (TW) .............................. 99106500 A (51) Int. Cl.
*A61C 3/02* (2006.01)
(52) U.S. Cl. ................ 433/76; 433/75; 606/96
(58) Field of Classification Search ............ 433/75, 433/76; 606/96; 408/115 B, 115 R; 409/86–91
See application file for complete search history.

(56) References Cited

U.S. PATENT DOCUMENTS

| | | | | |
|---|---|---|---|---|
| 1,321,130 A * | 11/1919 | Schlueter | | 433/76 |
| 1,380,040 A * | 5/1921 | Chayes | | 433/76 |
| 3,254,413 A * | 6/1966 | Suga | | 433/76 |
| 3,380,163 A * | 4/1968 | Westerman | | 433/76 |
| 4,344,755 A * | 8/1982 | Gold et al. | | 433/76 |
| 4,899,458 A * | 2/1990 | Minelli | | 33/644 |
| 5,741,133 A * | 4/1998 | Gordils et al. | | 433/76 |
| 6,926,525 B1 * | 8/2005 | Ronvig et al. | | 433/76 |

* cited by examiner

*Primary Examiner* — Cris L Rodriguez
*Assistant Examiner* — Edward Moran
(74) *Attorney, Agent, or Firm* — CKC & Partners Co., Ltd.

(57) ABSTRACT

A positioning assist device for drilling multiple dental implant holes is disclosed, which includes a main arm unit and an extension arm unit. The main arm unit has an arm body with two opposing ends, in which a reference shaft is pivoted on a first end, and an extension arm unit is pivoted on a second end via a connecting shaft. A drill-guiding portion having a drill-guiding hole is disposed on an external end portion of the second connecting head. The reference shaft is inserted into a first dental implant hole through an axis hole of the first end. The positions and angles of the drill-guiding hole of the extension arm unit can be adjusted to reach other dental implant holes by pivoting on the reference shaft and the connecting shaft, so as to lead a driller to drill other dental implant holes precisely according to the drill-guiding hole.

22 Claims, 6 Drawing Sheets

POSITIONING ASSIST DEVICE FOR DRILLING MULTIPLE DENTAL IMPLANT HOLES

RELATED APPLICATIONS

The present application is based on, and claims priority from, Taiwan Application Serial Number 99106500, filed Mar. 5, 2010, the disclosure of which is hereby incorporated by reference herein in its entirety.

BACKGROUND

1. Field of Invention

The present invention relates to a positioning assist device for drilling. More particularly, the present invention relates to a positioning assist device for drilling, multiple dental implant holes.

2. Description of Related Art

While tooth breaking, losing or extracting due to severe dental caries or other reasons, a dental implant (or an artificial tooth) is filled in the site of the missing tooth, so as to restore the appearance and integrity of teeth.

One of conventional dental restorations is a "carrying" way to fill a whole new dental implant. In brief, tops of two teeth adjacent to the missing tooth are grinded partially, a unit including the missing tooth and the flanking tooth bridge is made, and the unit is placed on the grinded tops of the adjacent teeth by adhering the flanking tooth bridge thereon. The adjacent teeth provide support to "carry" the dental implant in the site of the missing tooth.

The "carrying" way is cheap; however, it provides bad adhesion and injuries the adjacently health teeth, so that it is not a good dental restoration.

Hence, a dental implant surgery is widely applied in the dental industry and dental patients, in which the artificial tooth root is implanted rather than injuring the adjacent teeth.

As such for the dental implant surgery, it is to drill a hole of patient gums corresponding to the site of the missing tooth, to place and to fix a pre-made artificial tooth root into the hole. Thus, the quality of the dental implant depends on the precision of drilling position and angle.

During the conventional dental implant surgery, the drilling position and angle of the artificial tooth root depend on the experience of the dentist. However, the dentist is hard to control the precision, resulting in deviations of the drilling position, angle and the implanted tooth root. Therefore, the shifted tooth root cannot correspond to the adjacent teeth precisely, even resulting in failure of the dental implant surgery.

Thus, a positioning assist device for drilling is further developed, which places a reference rod, a guiding plate set and the like in the pre-drill position, for assuring the precision of the drilling position. However, when drilling multiple dental implant holes, the positioning assist device is necessary to place the reference rod, the guiding plate set and the like of the positioning assist device corresponding to each hole, resulting in more inconvenience.

For solving the above problem, a dental mold is pre-made according to the patient's gums, for subsequently drilling dental implant holes according to the dental mold. However, the cost of the dental mold and the waiting time of the dental implant will be increased.

Based on the above reasons, drilling multiple dental implant holes is still very inconvenient.

SUMMARY

Accordingly, an aspect of the present invention is to provide a positioning assist device for drilling multiple dental implant holes, which can drill holes and place dental implants at multiple sites, as well as assuring the precise position and angle of the dental implant, instead of making a dental mold structure.

Another aspect of the present invention is to provide a positioning assist device for drilling multiple dental implant holes with better application.

According to an embodiment, the present invention features a positioning assist device for drilling multiple dental implant holes, which includes a main arm unit, in which the main arm unit has an arm body with a first end and a second end disposed as opposed to each other, and the first end has a reference shaft pivoted thereon; and an extension arm unit pivoted on the second end of the main arm unit via a connecting shaft, in which the extension arm unit has a first connecting head, a pair of connecting rods, and a second connecting head all pivoted sequentially, an external end portion of the second connecting head has a drill-guiding portion disposed thereon, and the drill-guiding portion has a drill-guiding hole. The reference shaft is inserted and fixed into a desired position of a first dental implant hole for providing reference and support. Further, the positions and angles of the drill-guiding hole of the extension arm unit are adjusted to reach other dental implant holes by pivoting on the reference shaft and the connecting shaft, so as to lead a driller to drill other dental implant holes precisely through the drill-guiding hole.

In an embodiment, the main arm unit has a first position mechanism corresponding to the reference shaft, in which at least a first position indentation encircles the reference shaft at a height of the reference shaft, the arm body has a first through hole passing to the axis hole, and the first position mechanism includes: a first fixing screw bolt for fixing into the first through hole; a first spring disposed on a side of the first fixing screw bolt toward the axis hole; and a first position bead disposed on a side of the first spring toward the axis hole, in which the first position bead is elastically engaged with the first position indentation of the reference shaft. The first position indentations of the main arm unit at various heights are engaged with the first position head, so that the height of the main arm unit and the extension arm unit can be adjusted relatively and positioned.

In an embodiment, the first connecting head of the extension arm unit has a first connecting hole disposed therein vertically, the second end of the main arm unit has a second connecting hole disposed therein vertically, and the connecting shaft passes through and connects the first connecting hole and the second connecting hole; the main arm unit further has a second position mechanism corresponding to the connecting shaft, in which a second position indentation encircles the connecting shaft, the arm body has a second through hole passing to the second connecting hole, and the second position mechanism includes: a second fixing screw bolt for fixing into the second through hole; a second spring disposed on a side of the second fixing screw bolt toward the second connecting hole; and a second position bead disposed on a side of the second spring toward the second connecting hole, in which the second position bead is elastically engaged with the second position indentation of the connecting shaft. Therefore, the connecting shaft, the main arm unit and the extension arm unit are pivoted and positioned among them.

In an embodiment, the first connecting head has a first connecting trench flanked by a pair of first connecting arms, the pair of the first connecting arms have first pinholes at upper sites thereof and second pinholes at lower sites thereof respectively; the second connecting head has a second connecting trench flanked by a pair of second connecting arms, the pair of the second connecting arms have third pinholes at upper sites thereof and fourth pinholes at lower sites thereof respectively; the pair of the connecting rods include a first connecting rod and a second connecting rod disposed in parallel to each other and between the first connecting trench and the second connecting trench, a first pin and a third pin are pivoted on the first pinhole and the third pinhole respectively by passing through a first pivot hole and a third pivot hole at two ends of the first connecting rod respectively; and a second pin and a fourth pin are pivoted on the second pinhole and the fourth pinhole respectively by passing through a second pivot hole and a fourth pivot hole at two ends of the second connecting rod respectively. The first connecting head, the second connecting head, the first connecting rod and the second connecting rod are formed into a link mechanism with four-bar linkage, so as to adjust its position freely.

In an embodiment, the first connecting rod has a first length adjusting mechanism, so as to adjust the total length of the first connecting rod, as well as of the angle adjustment of the drill-guiding portion and the drill-guiding hole.

In an embodiment, the first length adjusting mechanism includes the first connecting rod that has a first adjusting rod and a third adjusting rod In an embodiment, the first connecting rod has a first securing mechanism for securing the first adjusting rod and the third adjusting rod. Therefore, the first connecting rod with the adjusted length is secured.

In an embodiment, the first securing mechanism includes: a first cover for capping the first adjusting rod and the third adjusting rod; and a first securing device disposed in the first cover, for forcing the third adjusting rod and the first adjusting rod tightly, so as to achieving a securing function.

In an embodiment, the first adjusting rod and the third adjusting rod are engaged together by first teeth disposed on adjacent surfaces thereof respectively, so as to make the first adjusting rod and the third adjusting rod to overlap more stably.

In an embodiment, scale marks are disposed on sides of the first adjusting rod and the third adjusting rod respectively, for estimating the length of the first connecting rod by the naked eye.

In an embodiment, the arm body has a second length adjusting mechanism and a second securing mechanism, for adjusting the whole length of the arm body and securing the arm body with the adjusted length.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

The foregoing and other technical content, characteristics and effects will now be made in detail to the present embodiments of the invention, examples of which are illustrated in the accompanying drawings.

Reference is made to FIGS. 1 to 7, which depict several diagrams of a structure of a positioning assist device for drilling multiple dental implant holes according to an embodiment of the present invention. The positioning assist device for drilling may include a main arm unit 100, an extension arm unit 200, a reference shaft 300 and a connecting shaft 400.

Figure 1:
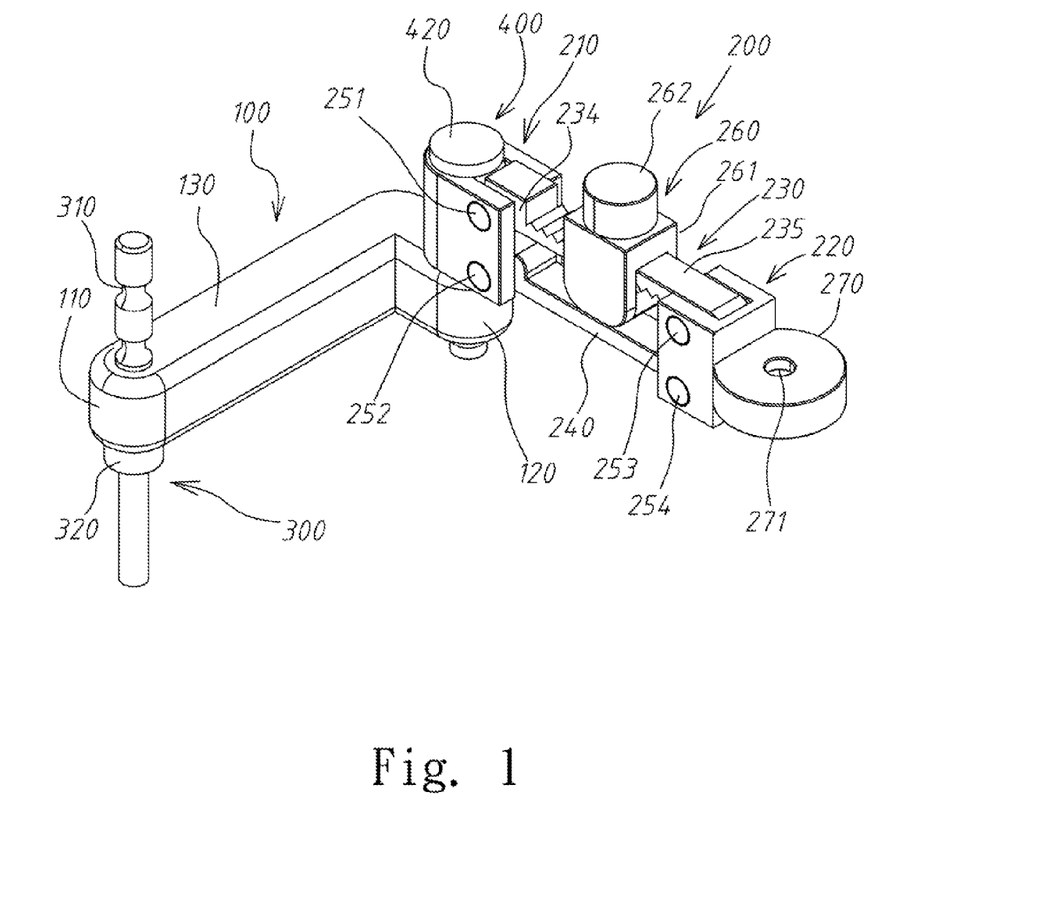
FIG. 1 depicts a three-dimensional diagram of a positioning assist device for drilling multiple dental implant holes according to an embodiment of the present invention.
Figures 2, 2A, 2B, 2C:
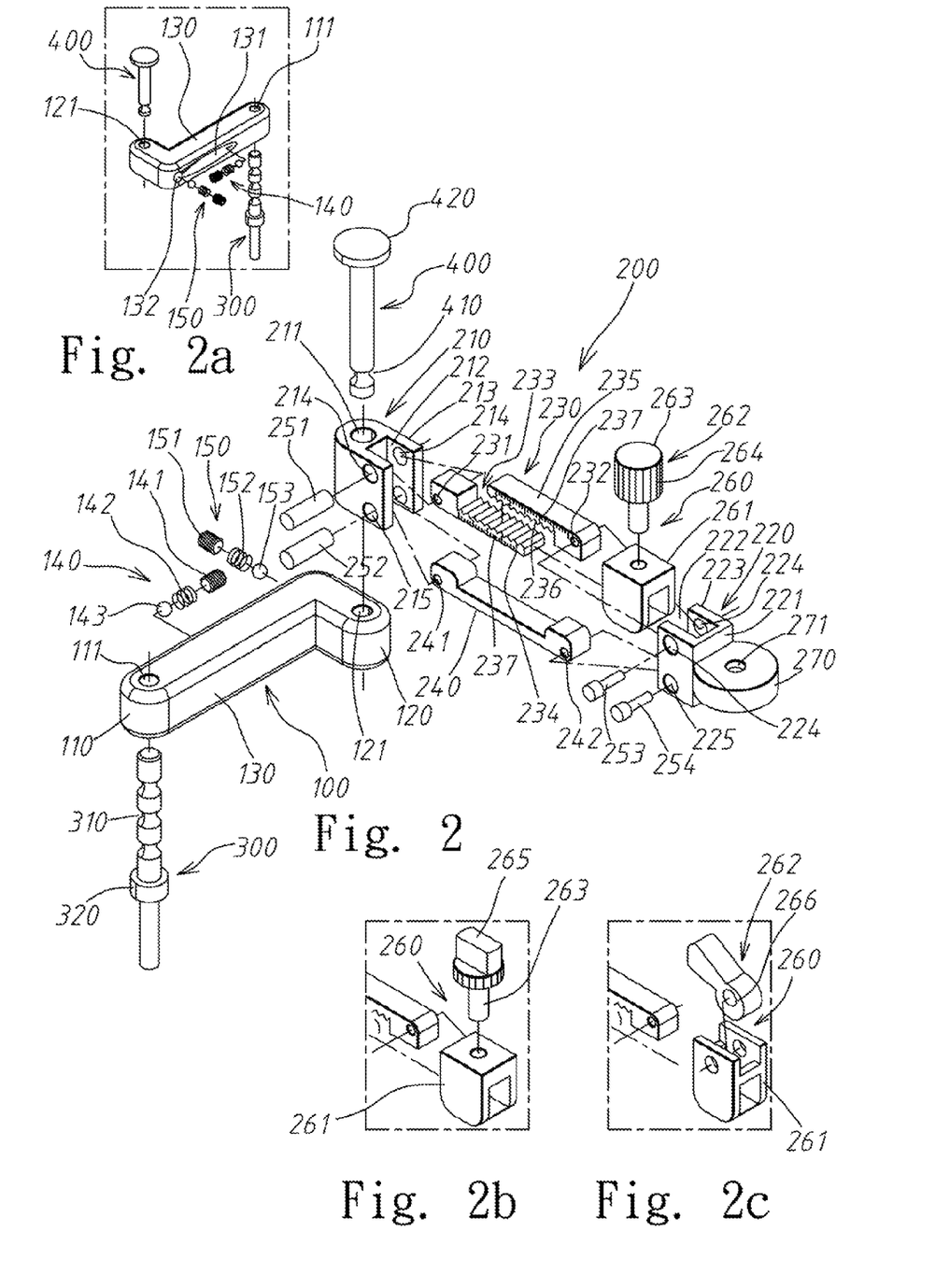
FIG. 2 depicts an explored diagram of a positioning assist device for drilling multiple dental implant holes according FIG. 1.
FIG. 2a depicts a diagram of a main arm unit of a positioning assist device for drilling multiple dental implant holes of FIG. 2 from another angle.
FIG. 2b depicts a diagram of a first securing mechanism of a positioning assist device for drilling multiple dental implant holes of FIG. 2 according to another embodiment of the present invention.
FIG. 2c depicts a diagram of a first securing mechanism of a positioning assist device for drilling multiple dental implant holes of FIG. 2 according to a further embodiment of the present invention.
Figure 3:
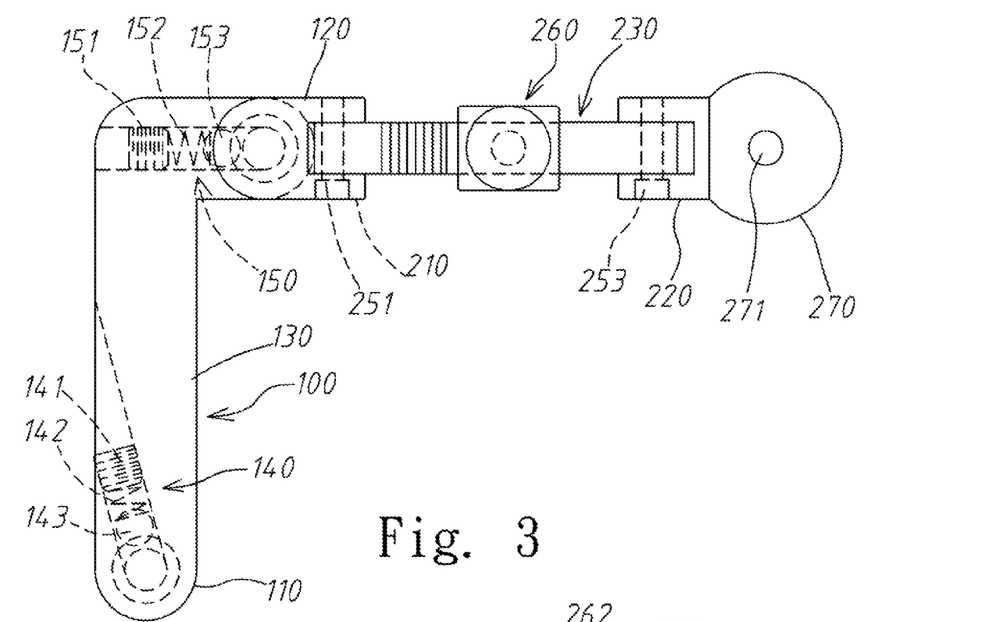
FIG. 3 depicts a top view of a positioning assist device for drilling multiple dental implant holes of FIG. 1.
Figure 4:
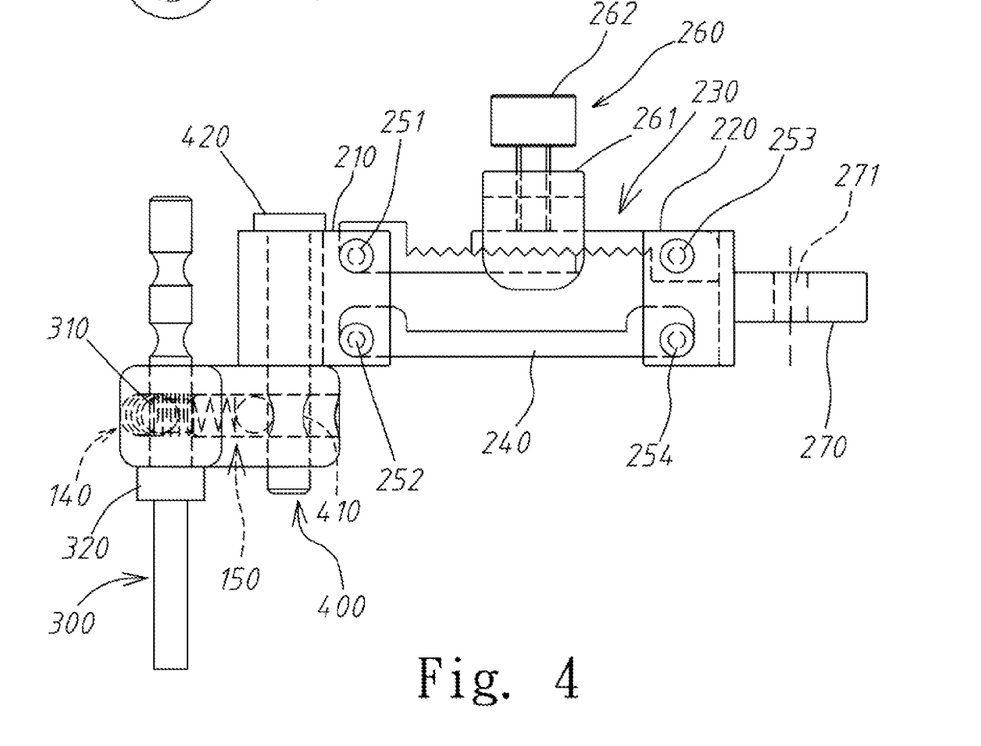
FIG. 4 depicts a side view of a positioning assist device for drilling multiple dental implant holes of FIG. 1.

The main arm unit 100 has an arm body 130 with a first end 110 and a second end 120 disposed as opposed to each other. The first end 110 of the main arm unit has an axis hole 111 disposed therein vertically for allowing the reference shaft 300 passing therethrough, and the main arm unit 100 has a first position mechanism 140 corresponding to the reference shaft 300.

Regarding the relationship between the first position mechanism 140 and the reference shaft 300, three first position indentations 310 may encircle the reference shaft 300 at various heights of the reference shaft 300, the arm body 130 of the main arm unit 100 has a first through hole 131 passing to the axis hole 111, and the first position mechanism 140 includes: a first fixing screw bolt 141, a first spring 142 and a first position bead 143. The first fixing screw bolt 141 is fixed into the first through hole 131; a first spring 142 is disposed on a side of the first fixing screw bolt 141 toward the axis hole 111; and a first position bead 143 is disposed on a side of the first spring 142 toward the axis hole 111, in which the first position bead 143 is elastically engaged with the first position indentation 310 of the reference shaft 300. The first position indentations 310 of the main arm unit 100 at various heights are engaged with the first position bead 143, so that the height of the main arm unit 100 and the extension arm unit 200 can be adjusted relatively and positioned.

The reference shaft 300 has a first stop collar 320 with an outer diameter larger than a diameter of the axis hole 111, and the first stop collar 320 is disposed below the first position indentation 310, for restricting a lower position of the main arm unit 100. The reference shaft 300 may be inserted and fixed in a first dental implant hole 610 pre-drilled in gums 600 of a patient, for positioning and supporting.

The extension arm unit 200 has a first connecting head 210, a pair of a connecting rod 230 and a connecting rod 240, and a second connecting head 220 all pivoted sequentially. The first connecting head 210 has a first connecting hole 211 disposed therein vertically, the second end 120 of the main arm unit 100 also has a second connecting hole 121 disposed therein vertically, and the connecting shaft 400 passes through and connects the first connecting hole 211 and the second connecting hole 121. Therefore, the main arm unit 100 and the extension arm unit 200 are formed into a bended arm structure, and they can stretch or bended freely by pivoting the reference shaft 300 and the connecting shaft 400, respectively.

The main arm unit 100 further has a second position mechanism 150 corresponding to the connecting shaft 400, in which the second position mechanism 150 has the same structure with the first position mechanism 140. With respect to the relationship between the second position mechanism 150 and the connecting shaft 400, a second position indentation 410 encircles the connecting shaft 400, the arm body 130 of the main arm unit 100 has a second through hole 132 passing to the second connecting hole 121, and the second position mechanism 150 includes: a second fixing screw bolt 151, a second spring 152 and second position bead 153. The second fixing screw bolt 151 is fixed into the second through hole 132; the second spring 152 is disposed on a side of the second fixing screw bolt 151 toward the second connecting hole 121; and the second position bead 153 is disposed on a side of the second spring 152 toward the second connecting hole 121, in which the second position bead 153 is elastically engaged with the second position indentation 410 of the connecting shaft 400. Once the connecting shaft 400 passes through the first connecting hole 211 of the extension arm unit 200 and the second connecting hole 121 of the main arm unit 100, the second position bead 153 of the second position mechanism 150 is automatically and elastically engaged with the second position indentation 410 of the connecting shaft 400, thereby quickly pivoting and positioning the connecting shaft 400, the main arm unit 100 and the extension arm unit 200.

The connecting shaft 400 has a second stop collar 420 with an outer diameter larger than a diameter of the first connecting hole 211, and the second stop collar 420 is disposed above the first connecting hole 211, for restricting the position of the extension arm unit 200 and preventing the extension arm unit 200 from leaving.

An implemented example is followed in the below to interpret the structure of the extension arm unit 200. The first connecting head 210 of the extension arm unit 200 has a first connecting trench 212 flanked by a pair of first connecting arms 213, the pair of the first connecting arms 213 have first pinholes 214 at upper sites thereof and second pinholes 215 at lower sites thereof respectively. The second connecting head 220 also has a second connecting trench 222 flanked by a pair of second connecting arms 223, the pair of the second connecting arms 223 have third pinholes 224 at upper sites thereof and fourth pinholes 225 at lower sites thereof respectively. The pair of the connecting rods include a first connecting rod 230 and a second connecting rod 240 disposed in parallel to each other and between the first connecting trench 212 and the second connecting trench 222. The first connecting rod 230 has a first length adjusting mechanism 233 for adjusting the length of the first connecting rod 230. A first pin 251 and a third pin 253 are pivoted on the first pinhole 214 of the first connecting head 210 and the third pinhole 244 of the second connecting head 220 respectively by passing through a first pivot hole 231 and a third pivot hole 232 at two ends of the first connecting rod 230 respectively. The second connecting rod 240 has a fixed length, and a second pin 252 and a fourth pin 254 are pivoted on the second pinhole 215 of the first connecting head 210 and the fourth pinhole 225 of the second connecting head 220 respectively by passing through a second pivot hole 241 and a fourth pivot hole 242 at two ends of the second connecting rod 240 respectively. Hence, the first connecting head 210, the second connecting head 220, the first connecting rod 230 and the second connecting rod 240 are formed into a link mechanism with four-bar linkage, so as to adjust its position freely.

An implemented example is followed in the below to interpret the first length adjusting mechanism 233 of the first connecting rod 230. The first connecting rod 230 has a first adjusting rod 234 and a third adjusting rod 235 overlapping to each other, the first pivot hole 231 is disposed at an external end of the first adjusting rod 234, and the third pivot hole 232 is disposed at an external end of the third adjusting rod 235. Thus, by adjusting the overlapping length of the first adjusting rod 234 and the third adjusting rod 235, the total length of the first connecting rod 230 is adjusted relatively, for further adjusting the angle of the drill-guiding portion 270 connected to the second connecting head 220.

Scale marks 237 are disposed on sides of the first adjusting rod 234 and the third adjusting rod 235 respectively, for aligning to the scale marks 237 and estimating the length of the first connecting rod by the naked eye. In addition, the first adjusting rod 234 and the third adjusting rod 235 are engaged together by first teeth 236 disposed on adjacent surfaces thereof respectively, so as to make the first adjusting rod 234 and the third adjusting rod 235 to overlap more stably.

For the purpose of stabilizing the adjusted length of the first connecting rod 230, the first connecting rod 230 has a first securing mechanism 260 for securing the first adjusting rod 234 and the third adjusting rod 235. In an implemented example, the securing mechanism includes a first cover 261 and a first securing device 262. The first cover 261 caps the first adjusting rod 234 and the third adjusting rod 235. The first securing device 262 is disposed in the first cover 261, for forcing the third adjusting rod 234 tightly engaged with the first adjusting rod 235, so as to fix to each other in a desired position.

In application, the first securing device 262 may be a screw bolt 263, and a plurality of slip-resistant grooves 264 are disposed on an outside of the screw bolt 263, for turning it tightly or loosely. Alternatively, a knob 265 may be disposed on a top of the screw bolt 263, for turning as the above manner.

The first securing device 262 may also be an eccentric toggle 266, and it is easier to turn it tightly or loosely by practicing the eccentric cam.

An external end portion 221 of the second connecting head 220 of the extension arm unit 200 hasp a drill-guiding portion 270 disposed thereon, and the drill-guiding portion 270 has a drill-guiding hole 271. After the position of the extension arm unit 200 and the length of the first connecting rod 230 are adjusted well the position and the angle of the drill-guiding hole 271 can be adjusted.

Figure 5:
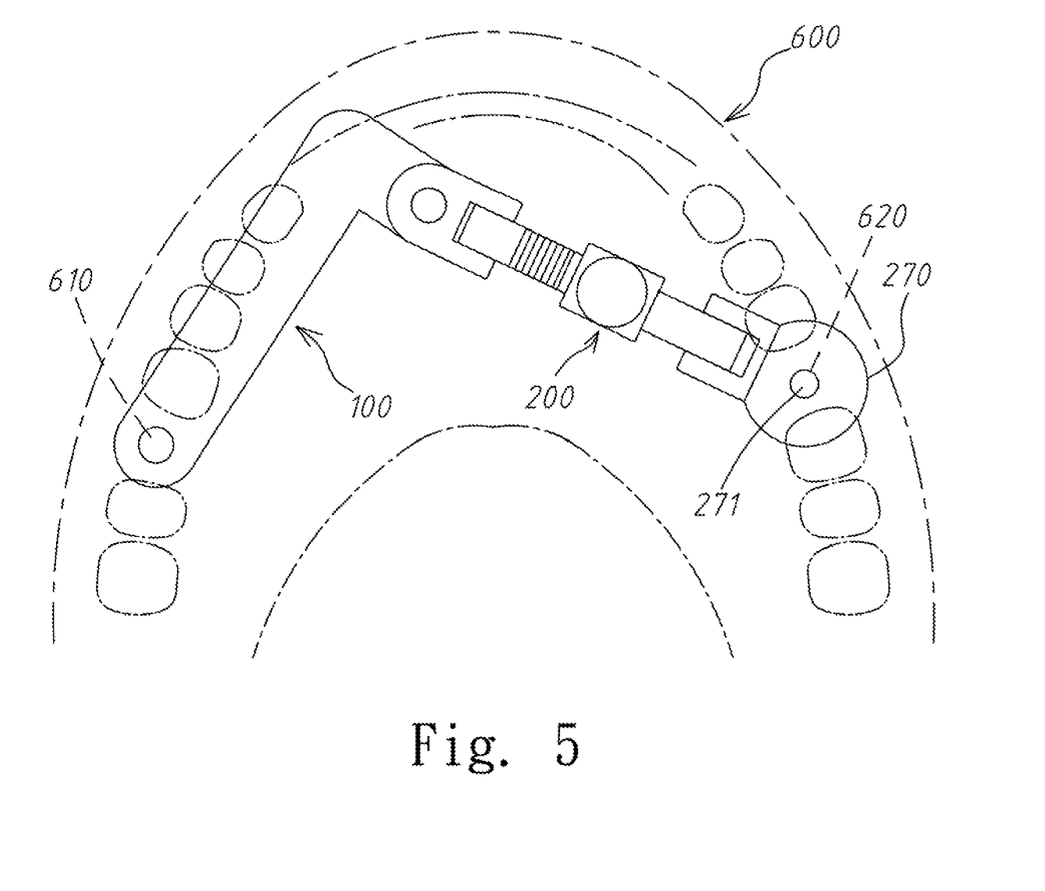
FIG. 5 depicts an assembling diagram of a positioning assist device for drilling multiple dental implant holes of FIG. 1.
Figures 6, 7:
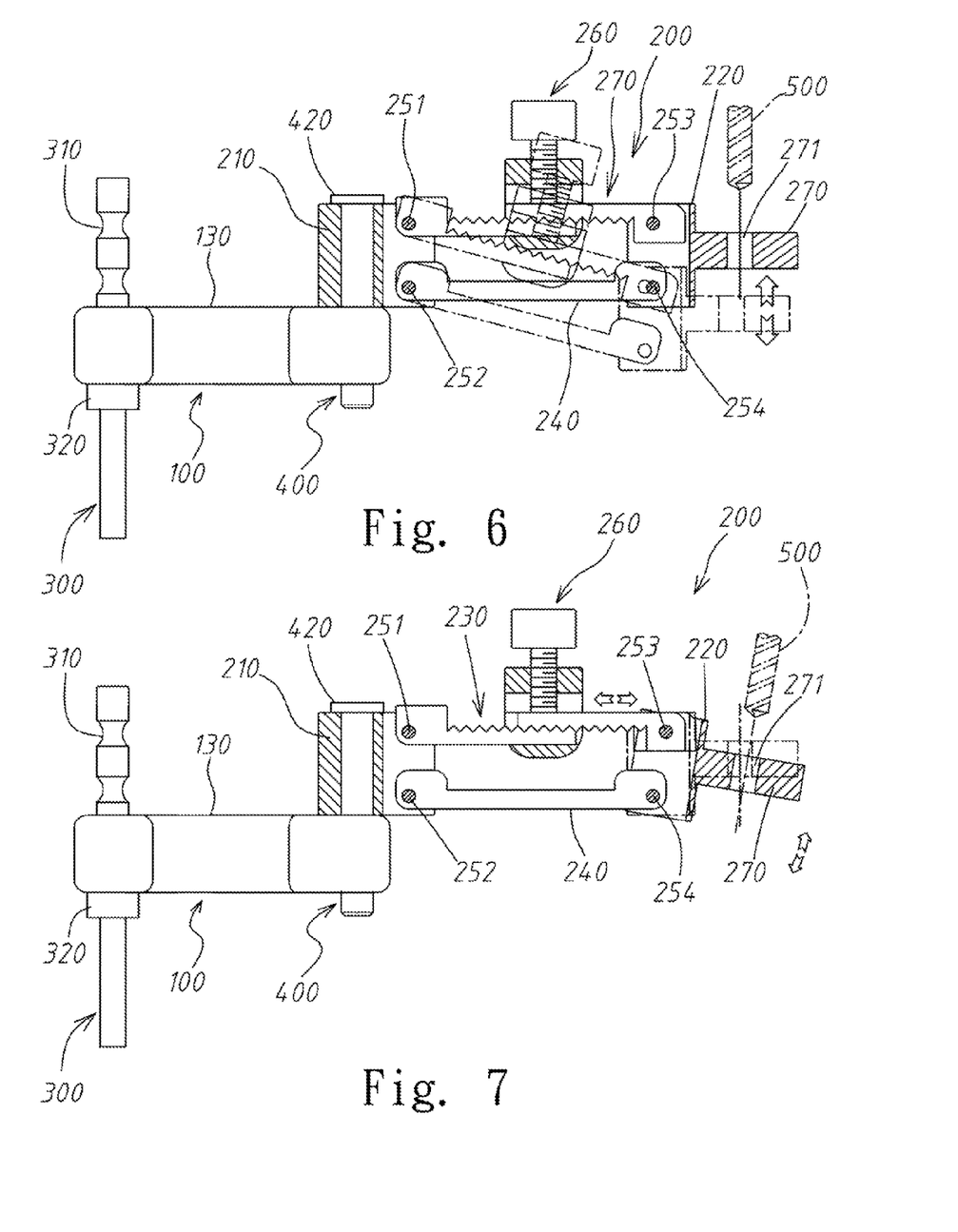
FIG. 6 depicts an operating diagram of a positioning assist device for drilling multiple dental implant holes of FIG. 1.
FIG. 7 depicts another operating diagram of a positioning assist device for drilling multiple dental implant holes of FIG. 1.

According to the positioning assist device for drilling multiple dental implant holes of an embodiment of the present invention, it is appropriately applied to drill multiple dental implant holes. Reference is made to FIGS. 5 to 7. While the positioning assist device of the present invention is applied to drill multiple dental implant holes, a first dental implant hole 610 is firstly drilled in the gums 600 of a patient by using conventional methods; next, the reference shaft 300 of the positioning assist device of the present invention is inserted and fixed in the first dental implant hole 610, for positioning and supporting; and then, the drill-guiding hole 271 of the extension arm unit 200 is adjusted to a second dental implant hole 620 by pivoting the reference shaft 300 and the connecting shaft 400; afterward, the length of the first connecting rod 230 is adjusted, thereby adjusting the angle of the drill-guiding portion 270 and the drill-guiding hole 271. Therefore, the position and the angle of the second dental implant hole 620 are adjusted easily, so as to lead a driller 500 to drill dental implant holes precisely through the drill-guiding hole 271. Following the similar manner as aforementioned, the position and the angle of the third dental implant hole, the fourth dental implant hole and so on are adjusted easily, too.

Figure 8:
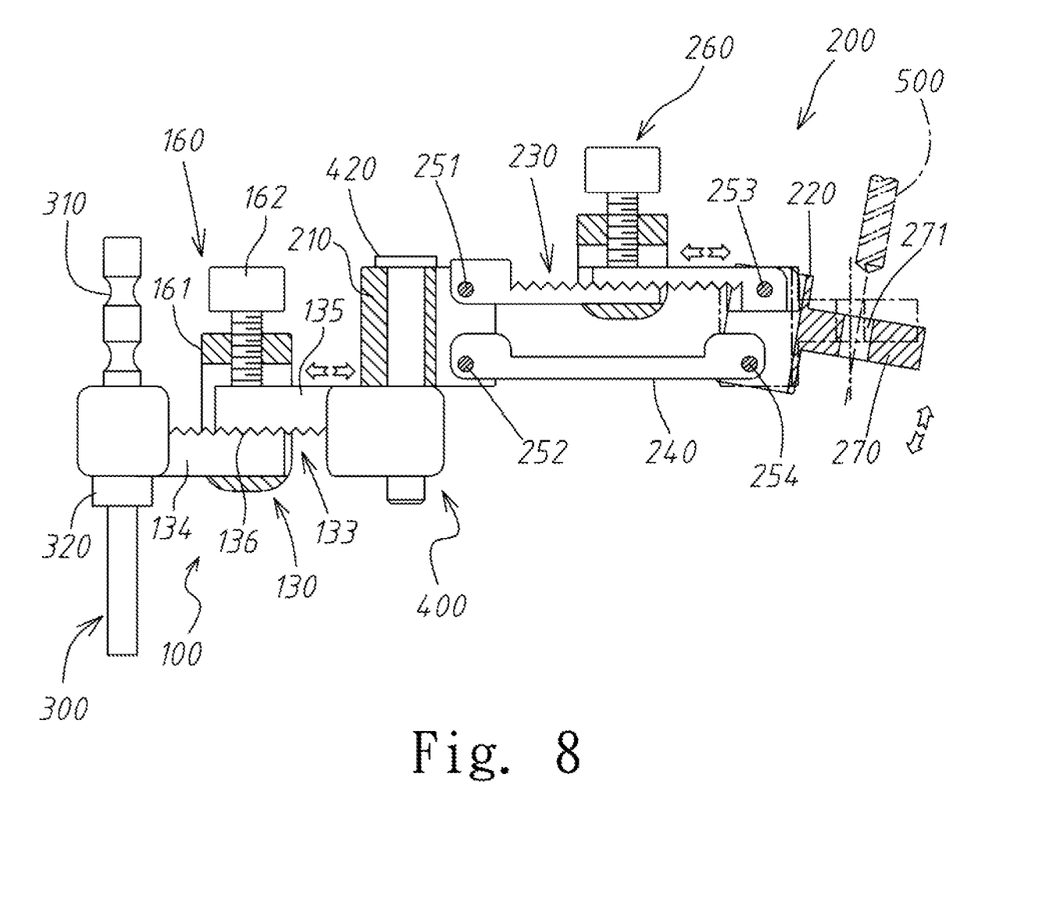
FIG. 8 depicts a further variant diagram of a positioning assist device for drilling multiple dental implant holes of FIG. 7 for showing the adjustable length of the arm body of the main arm unit.

Reference is made to FIG. 8. For the purpose of increasing the adjusting range of the positioning assist device, the arm body 130 of the main arm unit 100 further has a second length adjusting mechanism 133 that has a structure similar to the first length adjusting mechanism 233. In an implemented example, the arm body 130 has a first adjusting arm 134 and a second adjusting arm 135 overlapping to each other. An external end of the first adjusting arm 134 is formed to the first end 110, and the second adjusting arm 135 is formed to the second end 120. Thus, by adjusting the overlapping length of the first adjusting arm 134 and the second adjusting arm 135, the total length of the arm body 130 is adjusted relatively, for further adjusting the position of the extension arm unit 200 and the drill-guiding portion 270 connected to the arm body 130. In addition, the first adjusting arm 134 and the second adjusting arm 135 are engaged together by second teeth 136 disposed on adjacent surfaces thereof respectively, so as to make the first adjusting arm 134 and the second adjusting arm 135 to overlap more stably.

For the purpose of stabilizing the adjusted length of the arm body 130, the arm body 130 also has a second securing mechanism 160 for securing the first adjusting arm 134 and the second adjusting arm 135. The second securing mechanism 160 is structurally similar to the first securing mechanism 260 and includes a second cover 161 and a second securing device 162. The second cover 161 caps the first adjusting arm 134 and the second adjusting arm 135. The second securing device 162 is disposed in the second cover 161, for forcing the second adjusting arm 135 tightly engaged with the first adjusting arm 134, so as to fix to each other in a desired position.

Therefore, according to the positioning assist device for drilling multiple dental implant holes of an embodiment of the present invention, the position and the angle of the second dental implant hole and other holes are adjusted easily in the application of drilling multiple dental implant holes, for lead the driller to drill those dental implant holes precisely through the positioned drill-guiding hole. It overcomes troubles and inconvenience existed in the prior art, for example, complicated installations of the positioning assist device to each dental implant hole, and pre-made dental molds.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A positioning assist device for drilling multiple dental implant holes, comprising:
 a main arm unit, wherein the main arm unit has an arm body with a first end and a second end disposed as opposed to each other, and the first end has
  a reference shaft pivoted on the first end, wherein the first end of the main arm unit has an axis hole disposed therein vertically for allowing the reference shaft passing therethrough;
  a first position mechanism corresponding to the reference shaft;
  at least a first position indentation encircling the reference shaft at a height of the reference shaft, wherein the arm body has a first through hole passing to the axis hole, and the first position mechanism includes:
   a first fixing screw bolt for fixing into the first through hole;
   a first spring disposed on a side of the first fixing screw bolt toward the axis hole; and
   a first position bead disposed on a side of the first spring toward the axis hole, wherein the first position bead is elastically engaged with the first position indentation of the reference shaft; and
 an extension arm unit pivoted on the second end of the main arm unit via a connecting shaft, wherein the extension arm unit has a first connecting head, a pair of connecting rods, and a second connecting head all pivoted sequentially, a external end portion of the second connecting head has a drill-guiding portion disposed thereon, and the drill-guiding portion has a drill-guiding hole.

2. The positioning assist device for drilling multiple dental implant holes of claim 1, wherein the reference shaft has a first stop collar with an outer diameter larger than a diameter of the axis hole, and the first stop collar is disposed below the first position indentation.

3. The positioning assist device for drilling multiple dental implant holes of claim 1, wherein the first connecting head of the extension arm unit has a first connecting hole disposed therein vertically, the second end of the main arm unit has a second connecting hole disposed therein vertically, and the connecting shaft passes through and connects the first connecting hole and the second connecting hole.

4. The positioning assist device for drilling multiple dental implant holes of claim 3, wherein the main arm unit further has a second position mechanism corresponding to the connecting shaft.

5. The positioning assist device for drilling multiple dental implant holes of claim 4, wherein a second position indentation encircles the connecting shaft, the arm body has a second through hole passing to the second connecting hole, and the second position mechanism includes:
 a second fixing screw bolt for fixing into the second through hole;
 a second spring disposed on a side of the second fixing screw bolt toward the second connecting hole; and
 a second position bead disposed on a side of the second spring toward the second connecting hole, wherein the second position bead is elastically engaged with the second position indentation of the connecting shaft.

6. The positioning assist device for drilling multiple dental implant holes of claim 5, wherein the connecting shaft has a second stop collar with an outer diameter larger than a diameter of the first connecting hole, and the second stop collar is disposed above the first connecting hole.

7. The positioning assist device for drilling multiple dental implant holes of claim 3, wherein the first connecting head has a first connecting trench flanked by a pair of first connecting arms, the pair of the first connecting arms have first pinholes at upper sites thereof and second pinholes at lower sites thereof respectively; the second connecting head has a second connecting trench flanked by a pair of second connecting arms, the pair of the second connecting arms have third pinholes at upper sites thereof and a fourth pinholes at lower sites thereof respectively; the pair of the connecting rods include a first connecting rod and a second connecting rod disposed in parallel to each other and between the first connecting trench and the second connecting trench, a first pin and a third pin are pivoted on the first pinhole and the third pinhole respectively by passing through a first pivot hole and a third pivot hole at two ends of the first connecting rod respectively; and a second pin and a fourth pin are pivoted on the second pinhole and the fourth pinhole respectively by passing through a second pivot hole and a fourth pivot hole at two ends of the second connecting rod respectively.

8. The positioning assist device for drilling multiple dental implant holes of claim 7, wherein the first connecting rod has a first length adjusting mechanism.

9. The positioning assist device for drilling multiple dental implant holes of claim 8, wherein the first length adjusting mechanism includes the first connecting rod that has a first adjusting rod and a third adjusting rod overlapping to each other, the first pivot hole is disposed at an external end of the first adjusting rod, and the third pivot hole is disposed at an external end of the third adjusting rod.

10. The positioning assist device for drilling multiple dental implant holes of claim 9, wherein the first connecting rod has a first securing mechanism for securing the first adjusting rod and the third adjusting rod.

11. The positioning assist device for drilling multiple dental implant holes of claim 10, wherein the first securing mechanism includes:
   a first cover for capping the first adjusting rod and the third adjusting rod; and
   a first securing device disposed in the first cover, for forcing the third adjusting rod and the first adjusting rod tightly.

12. The positioning assist device for drilling multiple dental implant holes of claim 11, wherein the first securing device is a screw bolt.

13. The positioning assist device for drilling multiple dental implant holes of claim 12, wherein a plurality of slip-resistant grooves are disposed on an outside of the screw bolt.

14. The positioning assist device for drilling multiple dental implant holes of claim 12, wherein a knob is disposed on a top of the screw bolt.

15. The positioning assist device for drilling multiple dental implant holes of claim 11, wherein the first securing device is an eccentric toggle.

16. The positioning assist device for drilling multiple dental implant holes of claim 9, wherein the first adjusting rod and the third adjusting rod are engaged together by first teeth disposed on adjacent surfaces thereof respectively.

17. The positioning assist device for drilling multiple dental implant holes of claim 9, wherein scale marks are disposed on sides of the first adjusting rod and the third adjusting rod respectively.

18. The positioning assist device for drilling multiple dental implant holes of claim 8, wherein the arm body has a second length adjusting mechanism.

19. The positioning assist device for drilling multiple dental implant holes of claim 18, wherein the second length adjusting mechanism includes the arm body that has a first adjusting arm and a second adjusting arm overlapping to each other, an external end of the first adjusting arm is formed to the first end, and the second adjusting arm is formed to the second end.

20. The positioning assist device for drilling multiple dental implant holes of claim 19, wherein the arm body also has a second securing mechanism for securing the first adjusting arm and the second adjusting arm.

21. The positioning assist device for drilling multiple dental implant holes of claim 20, wherein the second securing mechanism includes:
   a second cover for capping the first adjusting arm and the second adjusting arm; and
   a second securing device disposed in the second cover, for forcing the second adjusting arm tightly engaged with the first adjusting arm.

22. The positioning assist device for drilling multiple dental implant holes of claim 19, wherein the first adjusting arm and the second adjusting arm are engaged together by second teeth disposed on adjacent surfaces thereof respectively.

* * * * *